(12) United States Patent
Bezuglov et al.

(10) Patent No.: US 12,012,375 B2
(45) Date of Patent: Jun. 18, 2024

(54) PROSTAGLANDIN F2 ALPHA DERIVATIVES FOR DECREASING INTRAOCULAR PRESSURE

(71) Applicant: GURUS BIOPHARM LIMITED LIABILITY COMPANY, Moscow (RU)

(72) Inventors: Vladimir Vilenovich Bezuglov, Moscow (RU); Igor Viktorovich Serkov, Noginsky (RU); Igor Ivanovich Lyubimov, Serpukhovsky (RU); Nataliya Mikhailovna Gretskaya, Moscow (RU)

(73) Assignee: GURUS BIOPHARM LIMITED LIABILITY COMPANY, Moscow (RU)

( * ) Notice: Subject to any disclaimer, the term of this patent is extended or adjusted under 35 U.S.C. 154(b) by 735 days.

(21) Appl. No.: 17/055,838

(22) PCT Filed: May 15, 2019

(86) PCT No.: PCT/RU2019/050062
§ 371 (c)(1),
(2) Date: Nov. 16, 2020

(87) PCT Pub. No.: WO2019/221641
PCT Pub. Date: Nov. 21, 2019

(65) Prior Publication Data
US 2021/0230111 A1    Jul. 29, 2021

(30) Foreign Application Priority Data

May 17, 2018   (RU) ............................ RU2018118157

(51) Int. Cl.
*C07C 405/00*   (2006.01)
*A61P 27/06*    (2006.01)
*C07D 207/08*   (2006.01)

(52) U.S. Cl.
CPC ........ *C07C 405/0041* (2013.01); *A61P 27/06* (2018.01); *C07D 207/08* (2013.01)

(58) Field of Classification Search
CPC ...................... C07C 405/0041; C07D 207/08
See application file for complete search history.

(56) References Cited

U.S. PATENT DOCUMENTS

| | | |
|---|---|---|
| 5,625,083 A | 4/1997 | Bezuglov et al. |
| 6,395,787 B1 * | 5/2002 | Woodward .............. A61P 27/06 |
| | | 564/189 |
| 7,910,767 B2 | 3/2011 | Ongini et al. |
| 8,101,658 B2 | 1/2012 | Benedini et al. |
| 2010/0130507 A1 | 5/2010 | Ongini et al. |

FOREIGN PATENT DOCUMENTS

| | | |
|---|---|---|
| FR | 2258372 | 8/1975 |
| JP | 49-69636 | 7/1974 |
| RU | 2 474 426 | 2/2013 |
| WO | 94/06433 | 3/1994 |
| WO | 01/58866 | 8/2001 |

OTHER PUBLICATIONS

International Search Report for PCT/RU2019/050062 dated Sep. 19, 2019, 3 pages.
Written Opinion of the ISA for PCT/RU2019/050062 dated Sep. 19, 2019, 3 pages.
Abstract of Woodward et al., "Intraocular pressure effects of selective prostanoid receptor agonists involve different receptor subtypes according to radioligand binding studies" *J Lipid Mediat.*, vol. 6 (1-3): 545-553 (Mar.-Apr. 1993).
Kozak et al., "Metabolism of Prostaglandin Glycerol Esters and Prostaglandin Ethanolamides in Vitro and in Vivo" *The Journal of Biological Chemistry*, vol. 276, No. 40: 36993-36998 (Oct. 5, 2001).
Nicolau et al., Bioactive Lipids (Eds. Nicolau A., Kokotos J.), Bridgewater: Oily Press, 2004—197 p.
Smith et al., "Prostaglandin and Thromboxane Biosynthesis" *Pharmac. Ther.*, vol. 49: 153-179 (1991).
Toh et al., "Molecular evolution of receptors for eicosanoids" *FEBS Letters*, vol. 361: 17-21 (1995).
Woodward et al., "The Pharmacology of Bimatoprost (Lumigan™)" *Survey of Opthalmology*, vol. 45, supp. 4: S337-S345 (May 2001).
Maddox Y.T. et al. Amide and I-amino derivatives of F prostaglandins as prostaglandin antagonists // Nature, Nature Publishing Group UK, vol. 273, Jun. 15, 1978, pp. 549-552.
Berglund B.A. et al. Investigation of structural analogs of prostaglandin amides for binding to and activation of CB1 and CB2 cannabinoid receptors in rat brain and human tonsils // Springer, US, vol. 469, Jan. 1, 1999, pp. 527-533.
Kuklev D.V. et al A new approach to mass spectrometry of oxygenated carbonic acids. Pyrrolidides // Bioorganicheskaya Khimia, 1994, 20(1), pp. 67-70 , Abstract in English provided.

* cited by examiner

*Primary Examiner* — Laura L Stockton
(74) *Attorney, Agent, or Firm* — Nixon & Vanderhye PC

(57) ABSTRACT

The invention relates to clinical chemistry, in particular, to new biologically active compounds—amide derivatives of prostaglandin F2α. These compounds have low cytotoxicity and are capable of stimulating formation of endogenous nitrogen oxide in mammal cells. Synthesis of such compounds promotes expansion of nomenclature of biologically active derivatives of prostaglandin F2α capable of reducing intraocular pressure.

1 Claim, 1 Drawing Sheet

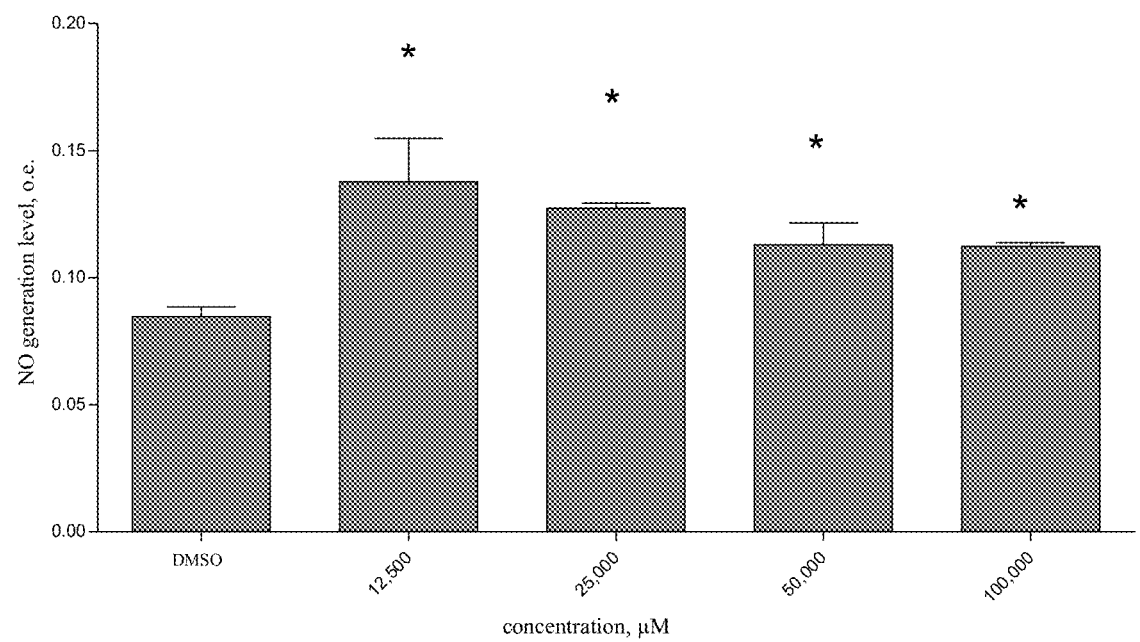

PROSTAGLANDIN F2 ALPHA DERIVATIVES FOR DECREASING INTRAOCULAR PRESSURE

This application is the U.S. national phase of International Application No. PCT/RU2019/050062 filed May 15, 2019 which designated the U.S. and claims priority to RU Patent Application No. 2018118157 filed May 17, 2018.

The invention relates to clinical chemistry, in particular, to new biologically active compounds—amide derivatives of prostaglandin $F_{2\alpha}$.

Prostaglandins are the family of multifunctional biologically active substances synthesized in organism from arachidonic acid by means of cyclooxygenase (COX). These oxidized fatty acids are autocrine and paracrine lipid mediators, and they are characterized by broad-spectrum of physiological activity, for example, combination of dilatator (bronchi smooth muscles), constrictor (gastrointestinal tract smooth muscles), antiaggregatory (platelets), hypo- or hypertensive activities [Nicolau A. In: Bioactive Lipids (Eds. Nicolau A., Kokotos J.)//Bridgewater: Oily Press, 2004.-197 p]. Prostaglandin $F_{2\alpha}$ is formed in organism as a result of arachidonic acid oxidative metabolism caused by cyclooxygenase at the first stage and by reductase—at the second stage of biosynthesis [Smith W. L., Marnett L. J., DeWitt D. L. Prostaglandin and thromboxane biosynthesis// Pharmacology & Therapeutics. 1991, V. 49(3), P. 153-179]. It is G-protein coupled receptor FP endogenous ligand, which activation results in intracellular calcium mobilization [Toh H, Ichikawa A, Narumiya S. Molecular evolution of receptors for eicosanoids.//FEBS Lett. 1995, V. 361, P. 17-21].

Prostaglandins are used for treatment of hypertension, thrombosis, asthma, gastric and intestinal ulcers, atherosclerosis prevention, and also in obstetrics. FP-receptor agonists are used in clinics as agents reducing intraocular pressure [Woodward D. F., Lawrence R. A., Fairbairn C. E., Shan T., Williams L. S. Intraocular pressure effects of selective prostanoid receptor agonists involve different receptor subtypes according to radioligand binding studies.//J Lipid Mediat. 1993, V. 6(1-3), P. 545-553.]

Prostamides (amides of prostaglandins and ethanolamine) are formed in organism by oxidation of arachidonic acid ethanolamide (anandamide) caused by cyclooxygenase-2 [Kozak K. R., Crews B. C., Ray J. L., Tai H. H., Morrow J. D., Marnett L. J. Metabolism of prostaglandin glycerol esters and prostaglandin ethanolamides in vitro and in vivo.//J. Biol. Chem. 2001, V.276(40), P. 36993-36998]. These derivatives appeared to be able to reduce intraocular pressure. The most known product of this class is synthetic analogue of prostamide F2—bimatoprost, wherein ethanolamine residue is replaced by ethylamine residue, and prostamide alkyl side chain is modified by introduction of phenyl radical [Woodward D. F., Krauss A. H., Chen J., Lai R. K., Spada C. S., Burk R. M., Andrews S. W., Shi L., Liang Y., Kedzie K. M., Chen R., Gil D. W., Kharlamb A., Archeampong A., Ling J., Madhu C., Ni J., Rix P., Usansky J., Usansky H., Weber A., Welty D., Yang W., Tang-Liu D. D., Garst M. E., Brar B., Wheeler L. A., Kaplan L. J. The pharmacology of bimatoprost (Lumigan)//Surv. Ophthalmol. 2001, V.45, Suppl 4, P. S337-S345].

There is known a variety of prostamide analogues, wherein as prostanoid as ethanolamine part of molecule is modified. The closest to the claimed compounds are prostamides capable of neuroprotection [V. V. Bezuglov, M. Y. Bobrov, N. M. Gretskaya, I. V. Serkov, G. N. Zinchenko, M. G. Akimov. Prostamides and their analogues capable of neuroprotection./Patent RU No. 2474426, priority on 26.12.2011, publication 10 Feb. 2013, Bulletin No. 4]. This patent describes prostamide E analogues comprising residues of nitroxyethylamine, glycine, gamma-aminobutyric acid, hydroxyethylamine, tyramine and dopamine. However, this patent does not describe analogues of prostamide F comprising the same modified residues of ethanolamine.

There also known the analogues of prostaglandin $F_{2\alpha}$, e.g. patent [U.S. Pat. No. 7,910,767], which describes ethers, thioethers and amides of prostaglandin $F_{2\alpha}$ with modified alkyl side chain, having the modified biological activity as compared to the known analogues of prostaglandin $F_{2\alpha}$, applied in the medical field (Bimatoprost, Travoprost, etc.).

There also known the analogues of prostaglandin $F_{2\alpha}$ comprising nitroxygroups.

U.S. Pat. No. 5,625,083 describes dinitroglycerol ethers of prostaglandins, including prostaglandin $F_{2\alpha}$, which could be used as vasodilators, antihypertensive agents, or bronchodilators.

U.S. Pat. No. 8,101,658 describes prostamides generating nitrogen oxide, which could be used for treatment of glaucoma and elevated intraocular pressure.

However, these inventions do not contain structures disclosed in this invention.

BRIEF DESCRIPTION OF DRAWINGS

FIGURE—Nitric oxide generation (measured as nitrite-ion by Griss's method) caused by prostaglandin F2a amide (3) in the concentration range from 25 up to 100 μM.

The object of this invention—expansion of nomenclature of biologically active derivatives of prostaglandin $F_{2\alpha}$, capable of reducing intraocular pressure. This problem is solved by synthesis of prostaglandin $F_{2\alpha}$ amide derivatives, wherein amide part is represented by amino acids, their nitro derivatives, cyclic amines and substituted ethanolamine.

Thus, the subject matter of this invention is amide derivatives of prostaglandin $F_{2\alpha}$ with the general formula (1):

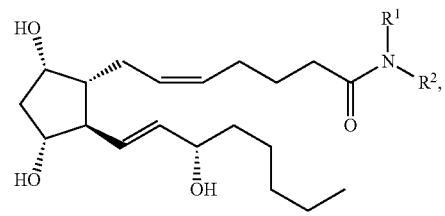

where

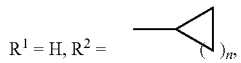

where n=1-4 or

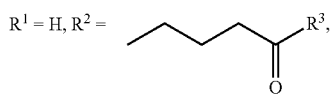

where

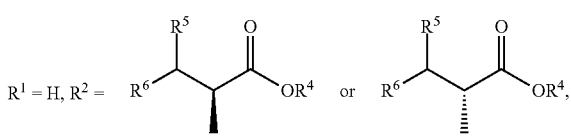

where
R⁴=H, CHMe₂; R⁵=H, OH; R⁶=H, OH, ONO₂, CH₂OH, CH₂ONO₂ or
R¹=H, R²=CH₂CH₂OC(O)NHCH₂CH₂ONO₂ or
R¹=H, R²=CH₂CH₂OC(O)OCH(CH₂ONO₂)₂ or

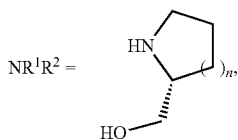

where n=1, 2 where $R^1$ and $R^2$ independently refer to hydrogen, alkyl, cycloalkyl, hydroxyalkyl, amino acids, ethers and amides of amino acids, and also $R^1+R^2$ could refer to heterocycle (e.g. substituted or unsubstituted piperidine, pyrrolidine, etc.); and also pharmaceutically acceptable salts for compounds with the general formula (1) with free carboxyl group; and also mixtures of two or more compounds with the general formula (1) in different ratios.

These substances have low cytotoxicity and are capable of stimulating formation of endogenous nitric oxide in mammal cells.

Unless otherwise specified, all technical and scientific terms used in this document have the same meaning, which is common in the art, and could be understood by those skilled in the art.

"Substituted" means that a specific group or residue includes one or more substituents different from hydrogen atoms.

"Unsubstituted" means that a specific group or residue does not comprise substituents different from hydrogen atoms.

"Alkyl" means unsubstituted alkyl group with linear or branched chain comprising from 1 to 6 carbon atoms.

"Cycloalkyl" means cyclic saturated hydrocarbon group with 3-6 ring carbon atoms (e.g. cyclopropyl, cyclobutyl and similar).

"Mixture"—co-inclusion of two and more substances without chemical bonding, and physical properties of each component are retained unchanged.

"Pharmaceutically acceptable salt" means that a component producing salt with a carboxyl group of the claimed substances will not cause harm to a human organism.

"Pharmaceutically acceptable cation" means that this cation will not cause harm to a human organism at salt formation.

Substances of this invention in a generic form could be synthesized by techniques known in the chemistry field. Some processes of producing the specific substances of this invention are illustrated in diagrams given in examples.

Biological activities of substances of this invention include absence of cytotoxicity up to concentration of 100 µM; ability to reduce intraocular pressure, ability to increase intracellular calcium concentration, ability to increase nitrogen oxide production.

The claimed substances, being analogues of natural prostaglandin $F_{2\alpha}$, are capable of interacting with specific prostanoid receptor FP, that results in stimulation of intracellular calcium mobilization.

Unexpected result of this invention is the ability of the claimed substances to induce endogenous synthesis of nitric oxide in mammal cells. Such properties have not been observed for any prostaglandin $F_{2\alpha}$ derivative. Moreover, compounds not comprising NO-donor groups, e.g. amide of prostaglandin $F_{2\alpha}$ with serine isopropyl ester (compound 3).

Therefore, the problem of this invention is solved by synthesis of new prostaglandin $F_2$ amide derivatives with the general formula (1), capable of inducing endogenous synthesis of nitric oxide, that significantly expands opportunities of medical application of the claimed substances due to involving endogenous regulator—nitrogen oxide into pharmacological effect mechanism.

The below examples are given to illustrate this invention, and they should not be considered as limiting the scope of the invention in any way.

Example 1. Prostaglandin $F_{2\alpha}$ Amides with Serine and its Derivatives, Cyclopropylamine and L-Prolinol

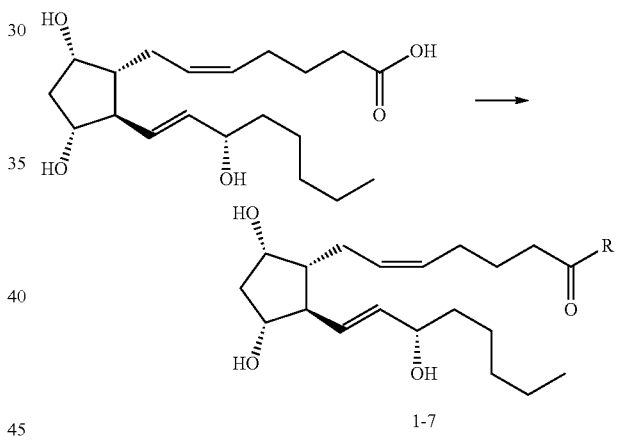

1-7

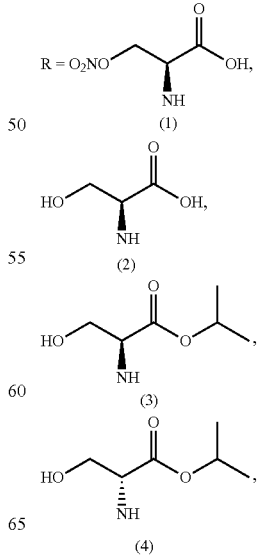

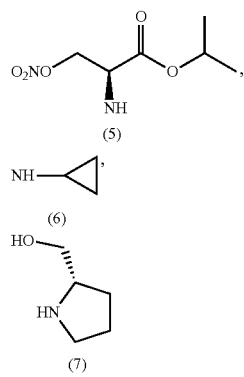

Prostaglandin $F_{2\alpha}$ Amide with L-Nitroserine (1).

Adding 76 μl (0.55 μmol) of $Et_3N$ to the solution of 150 mg (0.42 μmol) of prostaglandin $F_{2\alpha}$ in 2 ml of acetonitrile under an argon atmosphere, mixing within 5 minutes and adding the solution of 71 μl (0.55 μmol) isobutyl chloroformate in 500 μl of acetonitrile. Mixing the reaction mixture within 30 minutes at 4° C., evaporating to half of volume, diluting with 50 ml of ethyl acetate and washing with water (2×20 ml) and saturated water solution of NaCl (20 ml) and drying above anhydrous $Na_2SO_4$. Filtering the dryer, boiling down the filtrate in rotary evaporator under water-suction pump vacuum. Drying the residue in oil pump vacuum. Obtaining 171 mg of mixed anhydride, yellow oil.

Adding the solution of the obtained mixed anhydride in 1 ml of DMF and 52 μl of N-methyl morpholine to the solution of 104 mg (0.49 μmol) of L-nitroserine nitrate in 0.500 ml of DMF at 4° C. under an argon atmosphere, and mixing the obtained mixture within 90 minutes. Boiling down the solvent, diluting the residue with 50 ml of ethyl acetate and washing with 2M water solution of $NaHSO_4$ (20 ml) and saturated water solution of NaCl (20 ml) and drying above anhydrous $Na_2SO_4$. Filtering the dryer, evaporating the filtrate in rotary evaporator under water-suction pump vacuum. Obtaining 162 mg of prostaglandin F2a amide with L-nitroserine, yellowish oil, yield—70%.

PMR: 0.90 (3H), 1.29 (6H), 1.53 (3H), 1.75 (2H), 2.18 (7H), 2.41 (2H), 2.71 (1H), 3.95 (1H), 4.14 (2H), 4.33 (1H), 4.88 (2H), 5.52 (4H). Mass spectrum: 509.2832[M+Na]+, 441.3282 [M-NO2+Na+H]+, $[\alpha]_D^{25}=36.0°$, c=1, EtOH.

Prostaglandin $F_{2\alpha}$ Amide with L-Serine (2).

Derived similarly from prostaglandin $F_{2\alpha}$ and L-serine. Yield—51%. PMR: 0.84 (3H), 1.3 (6H), 1.52 (3H), 1.95 (3H), 2.16 (6H), 2.33 (2H), 2.68 (1H), 3.89 (2H), 3.92 (1H), 4.19 (1H), 4.32 (2H), 5.34 (4H), 7.8 (1H). $[\alpha]_D^{25}=33.5°$, c=1, EtOH:H2O, 1:2.

Prostaglandin $F_{2\alpha}$ Amide with L-Serine Isopropyl Ether (3).

Derived similarly from prostaglandin $F_{2\alpha}$ and L-serine isopropyl ether hydrochloride. Yield—57%. PMR: 0.89 (3H), 1.22 (6H), 1.3 (9H), 1.76 (3H), 2.04 (6H), 2.39 (2H), 3.9 (2H), 4.03 (2H), 4.13 (1H), 4.63 (1H), 5.08 (1H), 5.45 (4H), 6.83 (1H). $[\alpha]_D^{25}=28.4°$, c=1, EtOH.

Prostaglandin $F_{2\alpha}$ Amide with D-Serine Isopropyl Ether (4).

Derived similarly from prostaglandin $F_{2\alpha}$ and D-serine isopropyl ether hydrochloride. Yield—35%. PMR: 0.89 (3H), 1.21 (6H), 1.3 (9H), 1.74 (3H), 2.01 (6H), 2.4 (2H), 3.9 (2H), 4.0 (2H), 4.1 (1H), 4.6 (1H), 5.1 (1H), 5.43 (4H), 6.9 (1H). $[\alpha]_D^{25}=27.2°$, c=1, EtOH.

Prostaglandin $F_{2\alpha}$ Amide with L-Nitroserine Isopropyl Ether (5).

Derived similarly from prostaglandin $F_{2\alpha}$ and L-nitroserine isopropyl ether. Yield—64%. PMR: 0.84 (3H), 1.16 (6H), 1.23 (8H), 1.51 (4H), 1.96 (4H), 2.12 (4H), 3.88 (3H), 4.52 (1H), 4.9 (2H), 5.34 (5H), 7.9 (1H).

Prostaglandin F2α Amide with Cyclopropylamine (6).

Derived similarly from prostaglandin $F_{2\alpha}$ and cyclopropylamine. Yield—73%. PMR: 0.50 (2H), 0.78 (2H), 0.90 (3H), 1.31 (6H), 1.61 (4H), 1.86 (4H), 2.06 (4H), 2.36 (2H), 2.70 (1H), 4.00 (1H), 4.09 (1H), 4.20 (1H), 5.41 (1H), 5.57 (2H), 5.78 (2H). $[\alpha]_D^{25}=38.0°$, c=1, EtOH.

Prostaglandin F2a Amide with L-Prolinol (7).

Derived similarly from prostaglandin $F_{2\alpha}$ and L-prolinol. Yield—61%. PMR: 0.91 (3H), 1.36 (6H), 1.60 (6H), 1.89 (6H), 2.08 (4H), 2.39 (1H), 2.65 (1H), 3.2 (1H), 3.45 (1H), 3.57 (1H), 3.73 (1H), 3.90 (1H), 4.06 (1H), 4.21 (2H), 5.48 (2H), 5.69 (2H). $[\alpha]_D^{25}=22.0°$, c=1, EtOH.

Example 2. Amides of Prostaglandin $F_{2\alpha}$ with γ-Aminobutyric Acid Derivatives

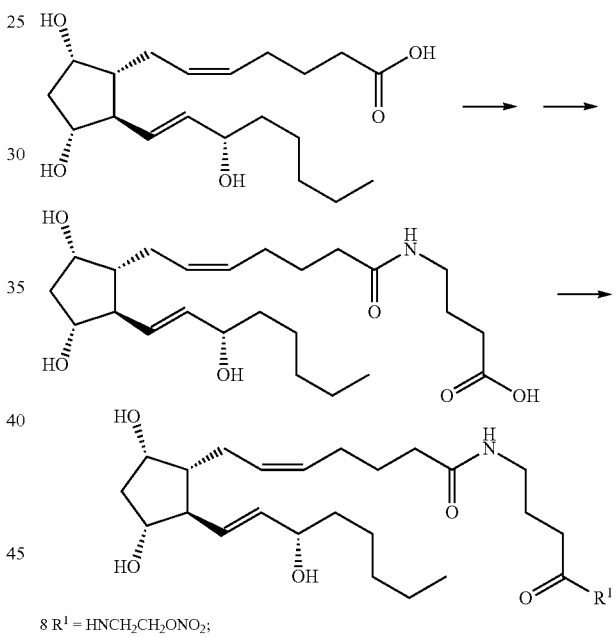

8 $R^1$ = $HNCH_2CH_2ONO_2$;
9 $R^1$ = $OCH_2CH_2ONO_2$;
10 $R^1$ = $CH(CH_2ONO_2)_2$

Amide of Prostaglandin $F_{2\alpha}$ with γ-Aminobutyric Acid.

Adding 600 μl of N,O-bis(trimethylsilyl) trifluoroacetamide to the solution of 103 mg (1.00 μmol) of γ-aminobutyric acid in 1 ml of acetonitrile and mixing within 18 hours at 23° C.

Adding 145 μl (1.05 μmol) of triethylamine and 125 μl (0.96 μmol) of isobutyl chloroformate to the solution of 284 mg (0.8 μmol) of prostaglandin $F_{2\alpha}$ in 3 ml of acetonitrile and mixing within 30 minutes at 23° C. Adding the obtained mixed anhydride to silylated γ-aminobutyric acid solution and mixing within 4 hours at 23° C. Adding methanol (5 ml) to the reaction mixture, mixing within 20 minutes and evaporated in rotary evaporator under water-suction pump vacuum. Dissolving the residue in ethyl acetate (20 ml) and washing with 2M water solution of $NaHSO_4$ (20 ml) and saturated water solution of NaCl (20 ml) and drying above anhydrous $Na_2SO_4$. Filtering the dryer, evaporating the filtrate in rotary evaporator under water-suction pump vacuum. Purifying the residue by silica gel column chromatography. Obtaining 132 mg of prostaglandin $F_{2\alpha}$ and γ-aminobutyric acid amide, clear oil, yield—60%. Mass spectrum, m/z: 462.2888 [M+Na]⁺.

Prostaglandin $F_{2\alpha}$ Amide with γ-Aminobutyric Acid Nitroethanolamide (8).

Adding 30 μl (0.23 μmol) of $Et_3N$ to the solution of 80 mg (0.18 μmol) of prostaglandin $F_{2\alpha}$ amide with γ-aminobutyric acid in 3 ml of acetonitrile under an argon atmosphere, mixing within 5 minutes and adding 30 μl (0.22 μmol) isobutyl chloroformate. Mixing the reaction mixture within 30 minutes at 4° C., adding the solution of 38 mg (0.37 μmol) of nitroetanolamine nitrate and 50 μl of $Et_3N$ in 2 ml of dichloromethane and mixing within 12 hours at 23° C. Boiling down the solvent, diluting the residue with 20 ml of ethyl acetate and washing with 2M water solution of $NaHSO_4$ (20 ml) and saturated water solution of NaCl (20 ml) and drying above anhydrous $Na_2SO_4$. Filtering the dryer, evaporating the filtrate in rotary evaporator under water-suction pump vacuum. Purifying the residue by silica gel column chromatography. Obtaining 35 mg of amide of prostaglandin $F_{2\alpha}$ with γ-aminobutyric acid nitroethanolamide (8), yield—36%. PMR: 0.88 (3H), 1.21 (6H), 1.65 (3H), 1.77 (4H), 2.11 (7H), 2.38 (1H), 2.62 (1H), 3.33 (2H), 3.55 (2H), 3.97 (1H), 4.18 (2H), 4.53 (2H), 4.68 (2H), 5.47 (4H). $[\alpha]_D^{25}=35.2°$, c=1, EtOH.

Prostaglandin $F_{2\alpha}$ Amide with γ-Aminobutyric Acid Nitroethylene Glycol Ether (9).

Adding 24 mg (0.12 μmol) of N-(3-dimethylaminopropyl)-N'-ethyl carbonate hydrochloride, 3 mg (0.02 μmol) of dimethylaminopyridine and 45 mg (0.1 μmol) of prostaglandin $F_{2\alpha}$ amide with γ-aminobutyric acid to the solution of 14 μl (0.12 μmol) of nitroethylene glycol in 1 ml of dichloromethane and mixing within 90 minutes at 23° C. Diluting the reaction mixture with chloroform (20 ml) and washing with 2M water solution of $NaHSO_4$ (20 mA), with water (2×20 ml) and with saturated water solution of NaCl (20 ml) and drying above anhydrous $Na_2SO_4$. Filtering the dryer, evaporating the filtrate in rotary evaporator under water-suction pump vacuum. Purifying the residue by silica gel column chromatography. Obtaining 20 mg of amide (9), white oil, yield—37%.

PMR: 0.89 (3H), 1.38 (11H), 1.88 (9H), 2.27 (2H), 2.87 (2H), 3.22 (2H), 3.81 (1H), 3.99 (1H), 4.07 (1H), 4.37 (2H), 4.67 (2H), 5.36 (4H), 7.57 (1H). $[\alpha]_D^{25}=24.0°$, c=1, EtOH.

Prostaglandin $F_{2\alpha}$ Amide with γ-Aminobutyric Acid Dinitroglycerol Ester (10).

Adding 44 mg (0.43 μmol) of N-(3-dimethylaminopropyl)-N'-ethylcarbodiimide hydrochloride in 0.5 ml of dichloromethane, 5 mg (0.04 μmol) of N-dimethylaminopyridine and 42 mg (0.22 μmol) of glycerol dinitrate to the solution of 84 mg (0.2 μmol) of prostaglandin $F_{2\alpha}$ amide with γ-aminobutyric acid in 1 ml of dichloromethane under an argon atmosphere, and mixing within 2 hours at 23° C. Evaporating the solvent, diluting the residue with ethyl acetate (20 ml) and washing with 2M water solution of $NaHSO_4$ (20 ml), with water (2×20 ml) and with saturated water solution of NaCl (20 ml) and drying above anhydrous $Na_2SO_4$. Filtering the dryer, evaporating the filtrate in rotary evaporator under water-suction pump vacuum. Purifying the residue by silica gel column chromatography. Obtaining 38 mg of prostaglandin $F_{2\alpha}$ amide with γ-aminobutyric acid dinitroglycerol ester (10), yield—33%. PMR: 0.84 (3H), 1.43 (14 H), 1.98 (8H), 2.34 (2H), 3.04 (2H), 3.88 (2H), 4.31 (1H), 4.46 (2H), 4.77 (2H), 5.36 (5H), 7.75 (1H). Mass spectrum, m/z: 626.2968 [M+Na]⁺, 586.3943 [M+H-H2O]⁺. $[\alpha]_D^{25}=30.2°$, c=1, EtOH Example 3. Prostaglandin $F_{2\alpha}$ Amide with 2-Aminoethyl-[2-(Nitroxy)Ethyl]Carbamate (11)

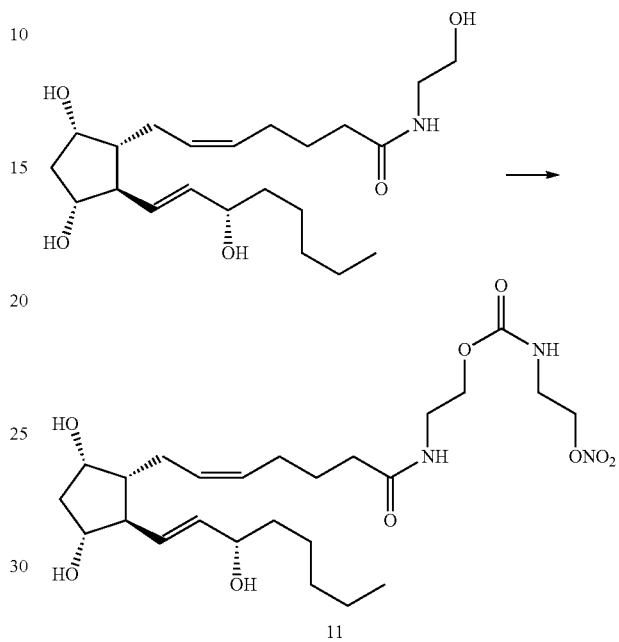

11

Adding 93 mg (0.37 μmol) of disuccinimidyl carbonate and 52 μl (0.37 μmol) of $Et_3N$ to the solution of 150 mg (0.37 μmol) of prostaglandin $F_{2\alpha}$ amide with ethanolamine in 3 ml of acetonitrile and mixing within 1.5 h at 23° C. Then, adding 62 mg (0.37 μmol) of nitroetanolamine nitrate and 37 mg (0.37 μmol) of $Et_3N$ and mixing within 18 hours at 4° C. Evaporating the solvent, diluting the residue with 20 ml of ethyl acetate and washing with 2M water solution of $NaHSO_4$ (20 ml) and saturated water solution of NaCl (20 ml) and drying above anhydrous $Na_2SO_4$. Filtering the dryer, evaporating the filtrate in rotary evaporator under water-suction pump vacuum. Purifying the residue by silica gel column chromatography. Obtaining 38 mg of amide (11), white oil, yield—19%. PMR: 0.90 (3H), 1.31 (6H), 1.55 (4H), 1.76 (3H), 2.15 (5H), 2.53 (2H), 3.34 (2H), 3.53 (2H), 4.01 (1H), 4.18 (4H), 4.56 (2H), 5.40 (2H), 5.57 (2H), 5.71 (1H), 6.25 (1H). Mass spectrum, m/z: 552.2983 [M+Na]⁺. $[\alpha]_D^{25}=34.6°$, c=1, EtOH Prostaglandin F2α Amide with 2-Aminoethyl-2-(Nitroxy)-1-[(Nitroxy)Methyl]Ethyl]Carbonate (12).

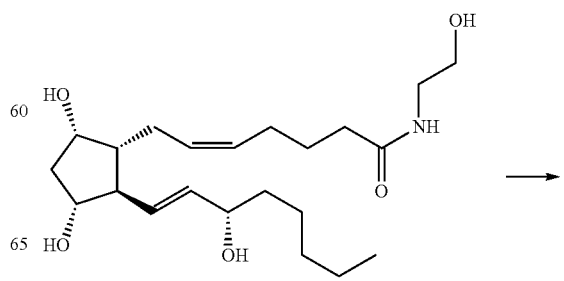

-continued

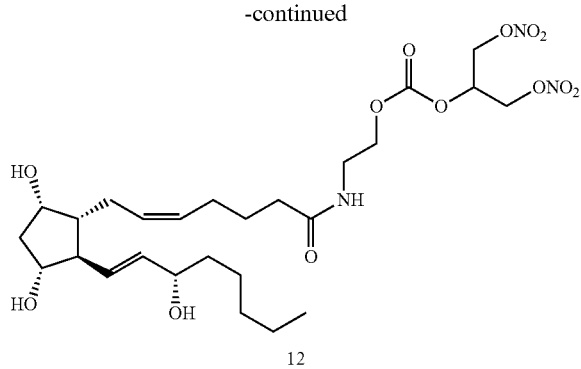

12

Adding 32 mg (0.12 μmol) of disuccinimidyl carbonate and 20 μl (0.14 μmol) of Et₃NK to the solution of 55 mg (0.14 μmol) of prostaglandin $F_{2\alpha}$ amide with ethanolamine in 1.5 ml of dichloromethane and mixing within 40 minutes at 23° C. Then, adding 25 mg (0.14 μmol) of glycerol dinitrate and 16 mg (0.14 μmol) of N-dimethylaminopyridine and mixing within 18 hours at 4° C. Evaporating the solvent, diluting the residue with 20 ml of ethyl acetate and washing with 2M water solution of NaHSO₄ (20 ml) and saturated water solution of NaCl (20 ml) and drying above anhydrous Na₂SO₄. Filtering the dryer, evaporating the filtrate in rotary evaporator under water-suction pump vacuum. Purifying the residue by silica gel column chromatography. Obtaining 20 mg of amide (12), white oil, yield—19%. PMR: 0.84 (3H), 1.24-1.53 (12H), 2.01 (8H), 2.39 (1H), 2.51 (1H), 2.64 (2H), 3.64 (2H), 4.00 (2H), 4.18 (1H), 4.46 (2H), 4.81 (2H), 5.31 (5H), 7.95 (1H). Mass spectrum, m/z: 628.2770 [M+Na]⁺, 588.2843 [M+H-H2O]⁺.

Example 4. Cytotoxic Activity of Prostaglandin $F_{2\alpha}$ Derivatives

3T3-L1 cells were incubated at 95% humidity, in the 5% CO₂ atmosphere, at 37° C. Cultivation was performed in DMEM medium comprising 7% FCS, 2 mM of glutamine, 100 U/ml of penicillin, 100 μg/ml of streptomycin and 0.25 μg/ml of amphotericin B. Cells were subcultured every 48-72 hours. For the purpose of suspending the cells were incubated in Versene's solution within 1 minute and in Trypsin-EDTA solution within 1 minute (0.25%).

Assessment of Substance Effect on Cell Culture

Cells were inoculated by 30 thousand into wells of 96-well plate (monolayer) in 100 μl of medium for MTT-test. After 24 hours of cultivation 100 μl of test substances in the medium used for cell culture were added to the cells with replacement of culture medium with a new one. Cells were incubated with test substances for 24 hours. Cells, to which 100 μl of medium used for cell culture were added to, were used as positive control.

Assessment of cell survival in the culture using the MTT assay After the incubation, the medium was removed from each well, and then 100 μl of MTT solution were added to each well (0.5 mg/ml of MTT, 3.5 mg/ml of D-glucose in Hanks' solution). The plate was placed into CO₂-incubator (Ependorf, Germany) for 1.5 h. After that, MTT was removed and 100 μl of DMSO were added to each well and mixed for 2 minutes in a shaker at 550 rpm. Then, the solution optical density was determined at the wavelength of 576 nm and 620 nm using a plate reader (EFOS 9305, OAO MZ Sapphir).

All test substances did not have noticeable cytotoxicity up to the concentration of 100 μM (Table 1).

TABLE 1

Cytotoxicity of prostaglandin $F_{2\alpha}$ derivatives relative to cultivated mice 3T3-L1 cells

| Compound number | Cytotoxicity, EC50 μM |
| --- | --- |
| 1 | 226.4 ± 2 |
| 2 | >200 |
| 3 | 143.6 ± 3 |
| 5 | 195.2 ± 2 |
| 6 | 124.4 ± 2 |
| 7 | 104.4 ± 2 |
| 8 | 193.9 ± 4 |
| 11 | 184.5 ± 3 |
| 20 | 137.5 ± 1.5 |

Example 5. Reducing Intraocular Pressure Caused by Prostaglandin $F_{2\alpha}$ Derivatives The study was performed on chinchilla rabbits with a mass of 2.5-3 kg. IOP was measured by automatic manual veterinary tonometer Tonovet (Icare, Finland).

2 groups of rabbets were used for testing each sample:

5 animals instilled with a single dose of sample into both eyes.

5 animals instilled with a single dose of normal saline into both eyes.

All test samples were instilled by 2 drops by a disposable pipette. IOP was measured before instillation and further, every hour within 6 hours. The results are given in Table 2. All tested substances were capable of reducing intraocular pressure in normotensive rabbits. This effect is more prominent for the compounds 3 and 6.

TABLE 2

Reducing intraocular pressure in normotensive rabbits after instillation of prostaglandin derivative solutions (maximum value of 5 animals' average data)

| Compound number | IOP reduction, mm Hg |
| --- | --- |
| 3 | 3.20 |
| 5 | 1.20 |
| 6 | 3.30 |
| 8 | 2.00 |
| 11 | 1.50 |
| 19 | 1.90 |

Example 6. Increasing of the Intracellular Calcium Concentration Caused by Prostaglandin F2a Derivatives 3T3-L1 cells were cultivated in DMEM medium with addition of 10% fetal calf serum (FCS), 4 mM of L-glutamine, 100 U/ml of penicillin, 100 μg/ml of streptomycin, 2.5 μg/ml of amphotericin B. Cells were cultured in the atmosphere of 5% CO₂, 95% humidity at 37° C.

Cell density at the time of experiment was 7000 per well of a 96-well plate, Calcium Green dye (1.5 mM, loading in 0.4% Pluronic F-62 in incubation medium without BSA for 1 hour at 37° C., triple washing of 200 μl of incubation medium after loading), incubation medium: Hanks' solution, 1 g/l of D-glucose, 1 mg/ml of fat-free BSA, introduction of substances in ethanol (<0.5% final concentration), incubation at 25° C., detecting at the excitation wavelength 485 nm, emission wavelength 535 nm.

Results

The addition of test substances to 3T3-L1 cells causes increase of intracellular calcium concentration. Thus, when adding reference substances: 67 µM of prostaglandin $F_{2\alpha}$ and prostamide F2 (prostaglandin $F_{2\alpha}$ ethanolamide), the calcium sensor fluorescence increases by 195 and 185 AU relative to control respectively for 10 minutes; while in the presence of the substance 3, such increase was 405 AU.

Example 7. Nitric Oxide Generation Caused by Prostaglandin F2α Derivatives

3T3-L1 cells were incubated at 95% humidity, in the 5% $CO_2$ atmosphere, at 37° C. Cultivation was performed in DMEM medium comprising 7% FCS, 2 mM of glutamine, 100 U/ml of penicillin, 100 µg/ml of streptomycin and 0.25 µg/ml of amphotericin B. Cells were subcultured every 48-72 hours. For the purpose of suspending the cells were incubated in Versene's solution within 2-3 minutes and in Trypsin-EDTA solution (0.25%).

Determination of NO Generation Level

Cells were inoculated by 30 thousand into wells (monolayer) of 96-well plate in 100 µl of medium. Incubation with substances lasted 20 hours. After that, medium aliquot was sampled from each well, and NO concentration was determined by modified Griess method. 12.5 µl of 0.04% sulfanilamide water solution were added to 75 µl of test medium in wells of 96-well plate for EIA, held within 10 minutes at room temperature protected from light, then, 12.5 µl of 2% naphthylethylenediamine solution in 3M of HCl were added, held again for 10 minutes at room temperature protected from light, then the optical absorption was determined at the wavelength of 540 nm.

Maximum activity of the most tested compounds by induction of nitrogen oxide generation was observed at the tested substance concentration of 100 µM. The results are given in Table 3.

TABLE 3

Nitrogen oxide (NO) generation by mice 3T3-L1 cells caused by prostaglandin $F_{2\alpha}$ derivatives at concentration of 100 µM.

| Compound number | NO generation, % to control |
|---|---|
| 1 | 7 |
| 2 | 25 |
| 3 | 15 |
| 6 | 5 |
| 7 | 15 |
| 8 | 22 |
| 11 | 28 |
| 20 | 57 |

However, for prostaglandin $F_{2\alpha}$ amide (3) the most effective concentration was 25 µM. At this concentration, nitric oxide level in 3T3-L1 cells increased by 60% relative to control indicated in the FIGURE.

The invention claimed is:

1. A compound selected from the following compounds:

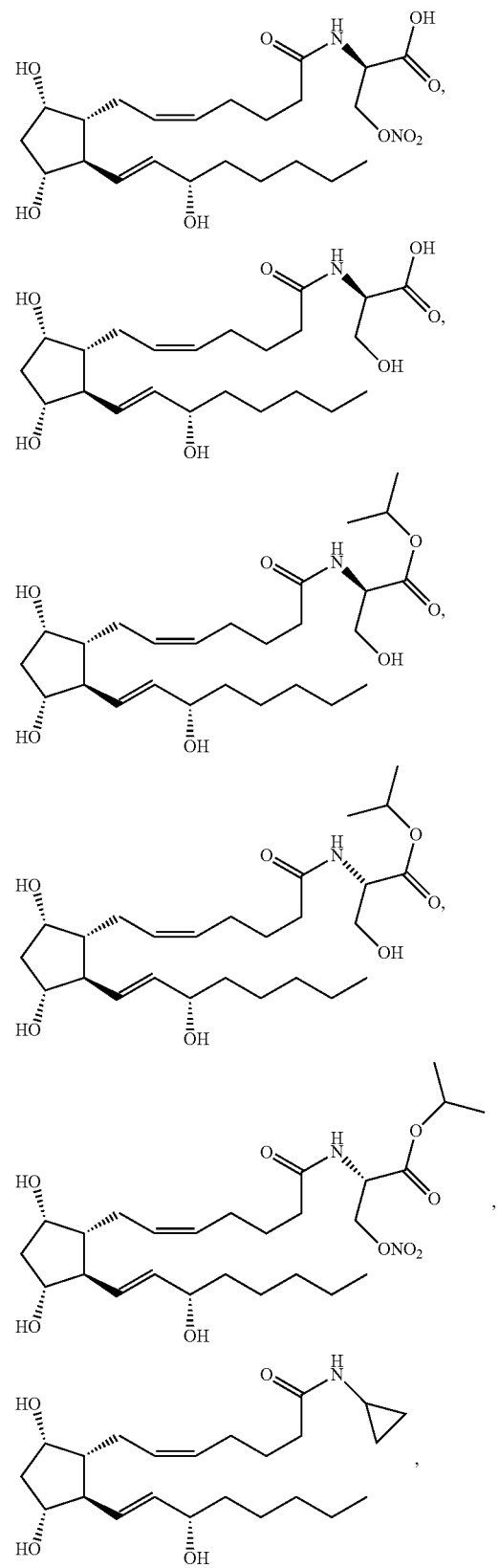

13
-continued
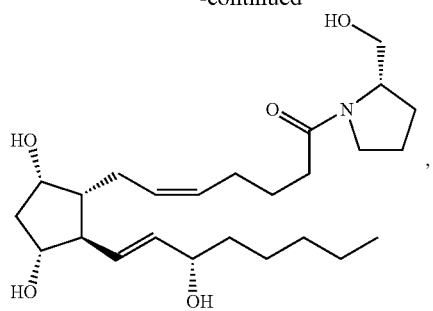
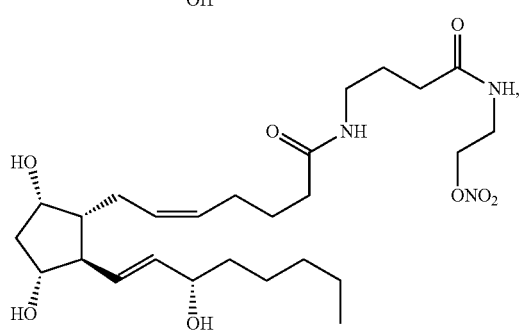
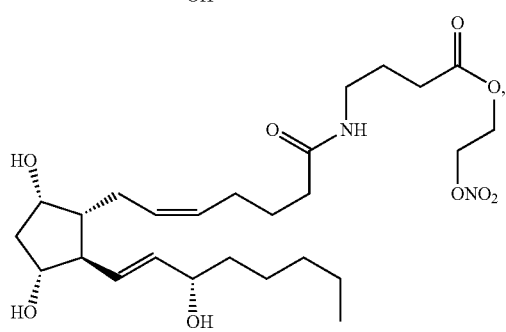
14
-continued
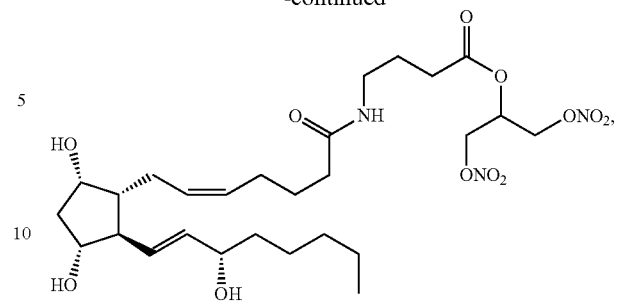
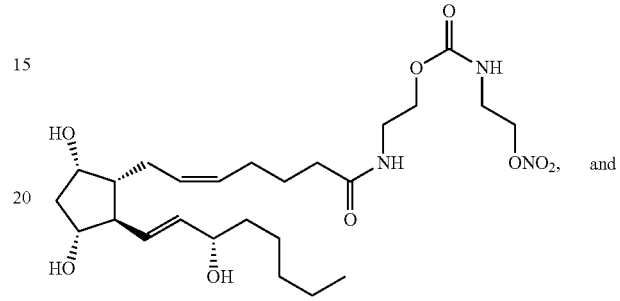
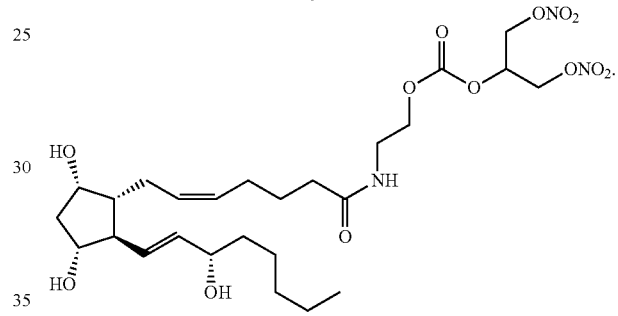
* * * * *